United States Patent [19]

Mills et al.

[11] Patent Number: 4,841,888
[45] Date of Patent: Jun. 27, 1989

[54] SEWING MACHINE

[76] Inventors: Timothy N. Mills, Flat 4, 45 Newman Street, London W.1.; Christopher P. Swain, 52 Gloucester Avenue, London NW1 8JD, both of England

[21] Appl. No.: 123,102

[22] Filed: Nov. 19, 1987

Related U.S. Application Data

[63] Continuation of Ser. No. 774,335, Sep. 10, 1985, abandoned.

[51] Int. Cl.⁴ .............................................. D05B 97/02
[52] U.S. Cl. .................................... 112/169; 112/199; 112/DIG. 2; 128/340
[58] Field of Search ...................... 112/80.03, 11, 165, 112/169, 197, 199, DIG. 2; 128/334 R, 340

[56] References Cited

U.S. PATENT DOCUMENTS

| | | | |
|---|---|---|---|
| 7,459 | 1/1877 | Turner | 112/197 X |
| 1,989,919 | 2/1935 | Everitt | 112/199 X |
| 2,637,288 | 5/1953 | Cerioni | 112/11 |
| 2,637,290 | 5/1953 | Sigoda | 112/197 X |
| 2,778,328 | 1/1957 | Doyen et al. | 112/11 |
| 2,945,460 | 7/1960 | Kagiyama | 112/169 |
| 4,107,953 | 8/1978 | Casillo | 112/80.03 X |
| 4,235,238 | 11/1980 | Ogiu et al. | 128/334 R |
| 4,350,160 | 9/1982 | Kolesov et al. | 128/334 R |
| 4,417,532 | 11/1983 | Yasukata | 112/169 |
| 4,484,580 | 11/1984 | Nomoto et al. | 128/340 |

FOREIGN PATENT DOCUMENTS

| | | | |
|---|---|---|---|
| 476676 | 9/1951 | Canada | 112/11 |
| 1685043 | 3/1971 | Fed. Rep. of Germany | |
| 59-146694 | 8/1984 | Japan | 112/11 |
| 645012 | 9/1984 | Switzerland | |
| 461673 | 2/1937 | United Kingdom | |
| 2050448 | 1/1981 | United Kingdom | |
| 2085934 | 5/1982 | United Kingdom | |

Primary Examiner—Wm. Carter Reynolds
Attorney, Agent, or Firm—Darby & Darby

[57] ABSTRACT

A sewing machine for forming stitches in a substrate, for example, in forming stitches in tissue during surgery, comprises a needle for passing thread into the substrate from one side thereof at a first location and for withdrawing the thread from the substrate at a second location spaced from the first location. The needle is removably operable solely from the said one side of the substrate. A stapling machine is also disclosed operating on similar principles for similar purposes.

11 Claims, 8 Drawing Sheets

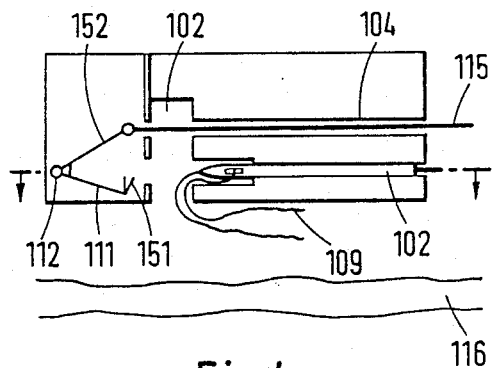
Fig.4a
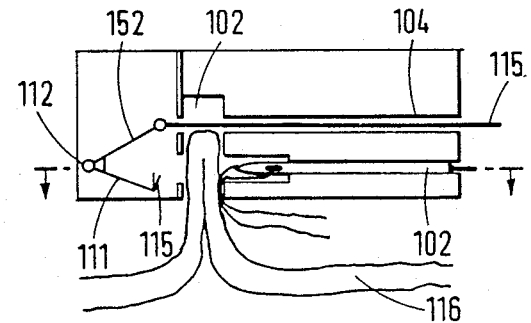
Fig.4b
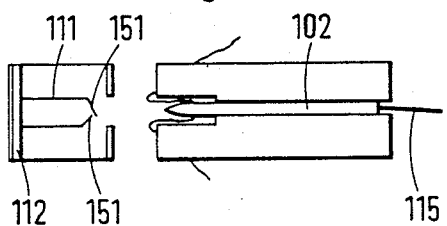
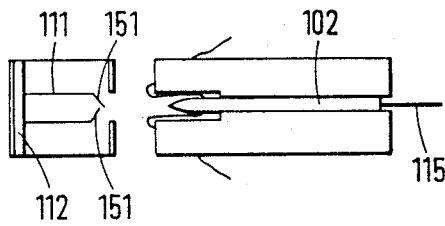
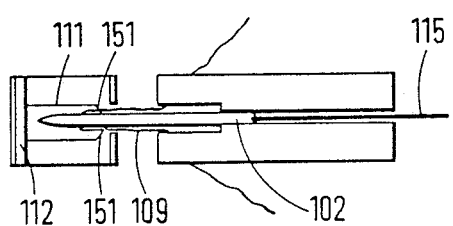
Fig.4c
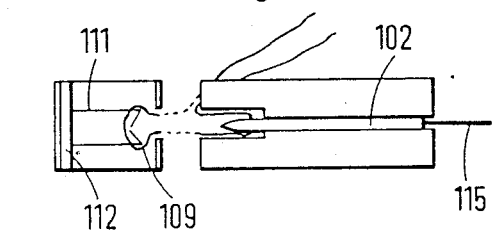
Fig.4d
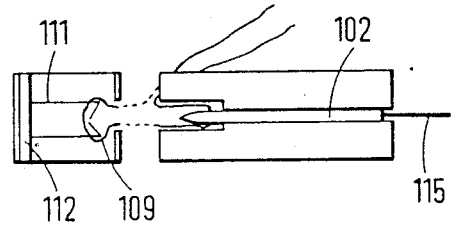

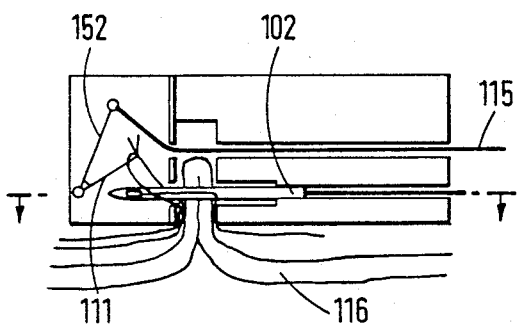
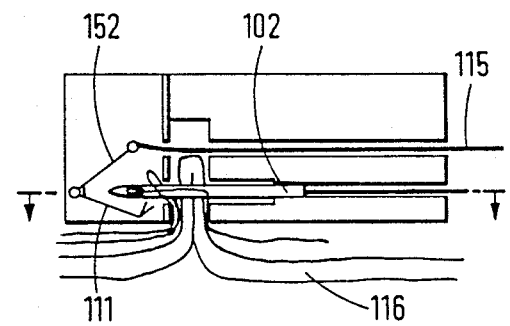
Fig.4e Fig.4f
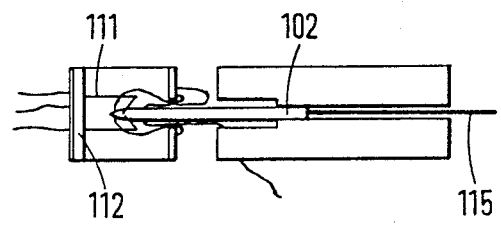
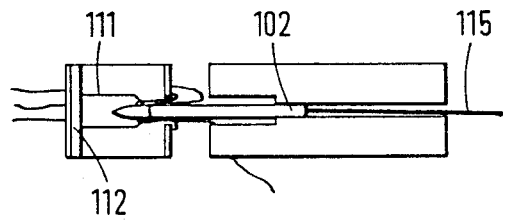
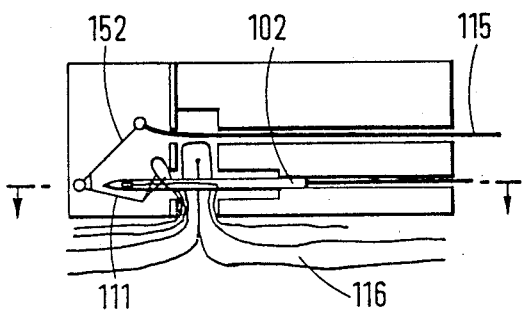
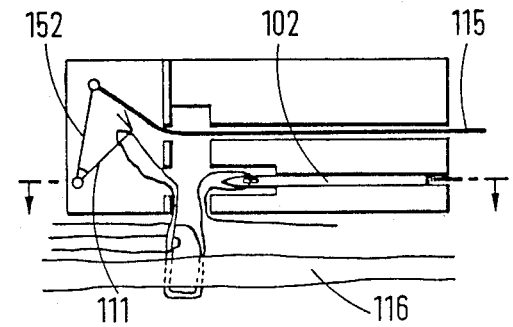
Fig.4g Fig.4h
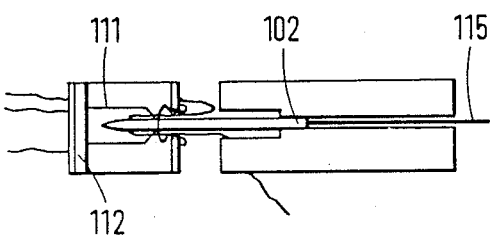
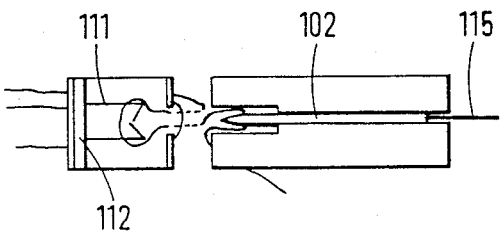

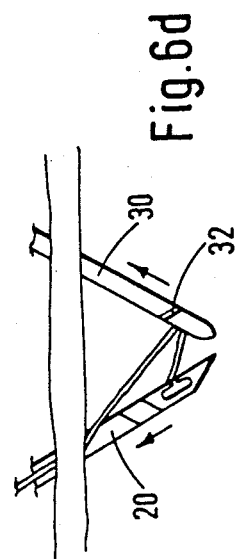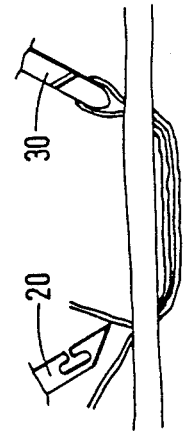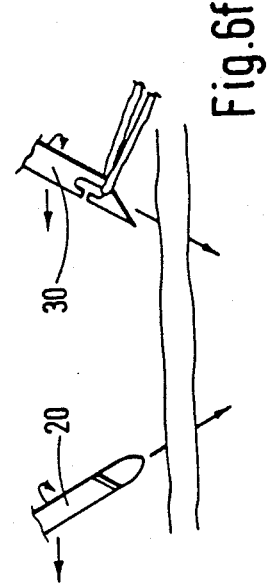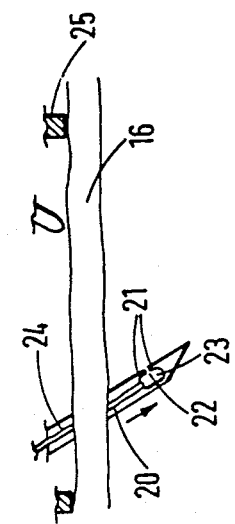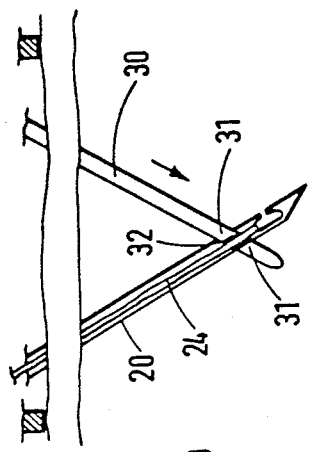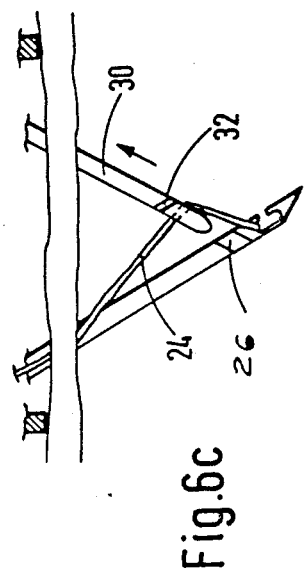

SEWING MACHINE

This is a continuation of application Ser. No. 774,335 filed Sept. 10, 1985, now abandoned.

FIELD OF THE INVENTION

This invention relates to sewing machines and stapling machines. The invention has particular application to sewing required in surgical procedures, and, more particularly, relates to sewing and stapling machines which can be used inside the body of a patient without the need to make an external incision in the patient, the machine being controlled externally of the patient, for example by endoscopic means. For convenience such a machine is referred to below as an endoscopic sewing or stapling machine, and the ensuing description relates largely to endoscopic sewing and stapling machines. It is to be understood, however, that sewing and stapling machines according to the present invention could be used in other applications.

BRIEF SUMMARY OF THE INVENTION

According to one aspect of the present invention there is provided a sewing machine for forming stitches in a substrate, comprising means for passing a thread into the substrate from one side thereof at a first location and for withdrawing the thread from the substrate at a second location spaced from the first location, the said means being remotely operable solely from the said one side of the substrate.

According to another aspect of the invention there is provided a stapling machine operating on similar principles. The machines according to the present invention open up the possibility of performing a wide range of internal surgical procedures without having to make an external incision in the patient. Potential medical uses of such machines could include the oversewing of bleeding or perforated ulcers, the oversewing of bleeding varices, the narrowing of lax internal anatomical sphincters or organs, the closure of internal holes or fistulae, the assistance in the removal of normal or abnormal tissue, and the attachment of materials or objects to the walls of tissue (for example for attaching gastric tubes for feeding purposes to the wall of the stomach, or for attaching X-ray opaque markers to mark the site of, say, a cancer, or for attaching a piece of material containing a drug to permit localised internal treatment).

BRIEF DESCRIPTION OF THE DRAWINGS

FIGS. 4a to 4h show diagrammatically the second embodiment of sewing machine in successive stages of operation, each Figure comprising two longitudinal sections through mutually perpendicular planes, in order to enable the operation of the machine to be more easily visualised in three dimensions, one of the longitudinal sections in each Figure being taken along the section line indicated in the other;

FIGS. 6a to 6f show a third embodiment of the present invention in successive stages of operation;

DESCRIPTION OF PREFERRED EMBODIMENTS

Figure 1A:
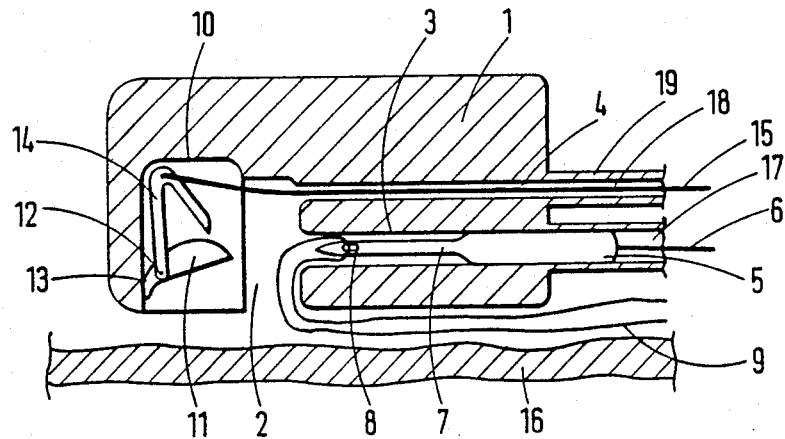
FIGS. 1a, 1b and 1c show a first embodiment of a sewing machine according to the present invention, in three successive stages of operation.
Figure 1B:
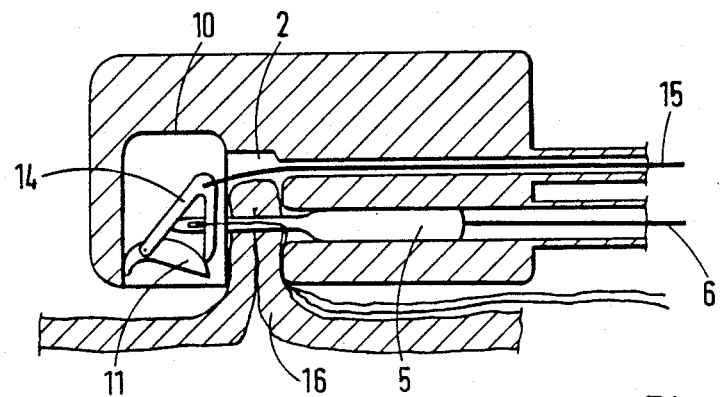
Figure 1C:
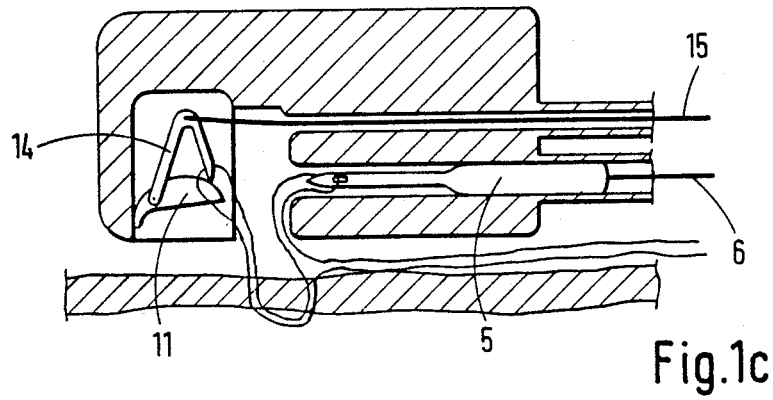

The embodiment shown in FIGS. 1a to 1c comprises a block 1 preferably formed of a transparent material such such as perspex. A slot 2 is formed in the block 1, the slot extending from the front to the back of the block, i.e. in a direction perpendicular to the plane of the paper. The block also has two longitudinal channels 3 and 4 formed therein. The channel 3 receives a needle 5 which is longitudinally slidable in the channel 3 under the control of a control wire 6. The needle 6 has a head portion 7 in which is formed an eye 8, and a thread 9 to be used in sewing is passed through the eye 8. The channels 3 and 4 are continuous with corresponding channels 17 and 18 formed in a two-channel endoscope tube 19.

The block 1 also has a compartment 10 formed therein, distal to the slot 2. A shoe 11 is pivotally mounted in the compartment 10 by means of the flexible portion 13. The rear portion 13 of the shoe 11 is also resilient and serves to bias the shoe in an anti-clockwise direction into the position shown in FIG. 1a. A hook 14 is mounted on the shoe 11 by means of a pin 12 for pivotal movement about the pin 12 and with respect to the shoe 11. The hook 14 is approximately in the shape of a V, and a control wire 15, which passes down the channels 4 and 18, is attached to the hook 14 adjacent the vertex of the V. A source of suction (not shown) is connected to the proximal end of channel 18 for a purpose which will be described below.

Turning now to the operation of the machine, the initial position is shown in FIG. 1a, with the machine positioned above a layer of tissue 16 in which it is desired to form stitches. Suction is then applied to the slot 2 to suck into the slot a double layer of tissue, as can be seen in FIG. 1b. The depth of the slot 2 controls the amount of tissue which is sucked in. The needle 5 is then forced forwards through the double layer of tissue, as is also shown in FIG. 1b. The needle carries with it the loop of thread 9. The tip of the needle strikes the shoe 11 which is thereby caused to pivot downwardly against the biassing force of the shoe portion 13. The control wire 15 is then pulled rightwardly to cause the hook 14 to pivot and thereby catch the loop of thread carried by the eye 8 of the needle 5. This can also be seen in FIG. 1b. It should be mentioned at this point that the side of the head portion 7 of the needle has a groove (not shown) formed therein to allow the hook 14 to pass between the head portion 7 and the thread carried thereby.

As shown in FIG. 1c the needle is then withdrawn leaving the loop of thread held between the hook 14 and the shoe 11. The suction applied to the slot 2 is then released and the double layer of tissue leaves the slot. This is also shown in FIG. 1c, from which it can be seen that the effect of the steps described above is to pass a loop of thread from one side of the tissue through the tissue at a first location and back out of the tissue on the same side at a second location from the first location. As will be appreciated, this has been done without requiring access to the opposite side of the tissue which one would expect to be inaccessible under normal circumstances.

Figure 2:
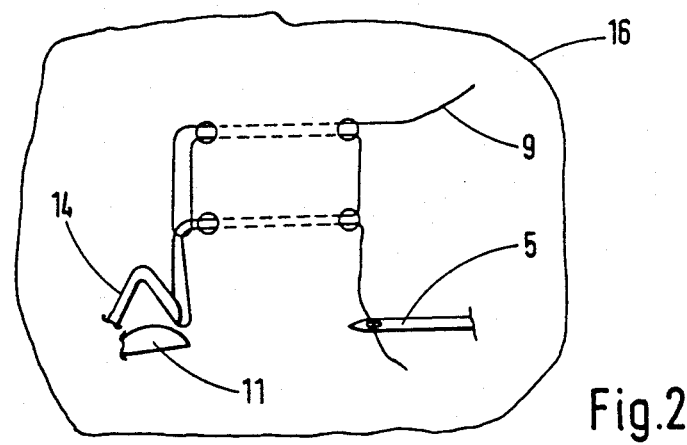
FIG. 2 shows, by way of example, one stitch pattern which can be formed by the machine of FIGS. 1a to 1c.

The machine is then moved to the site of the next stitch, suction is re-applied and the needle passes through a double layer of tissue at a different point. It is possible to form a variety of different stitches using the machine, but one example is shown diagrammatically in FIG. 2. This stitch pattern is formed by moving the machine between successive stitches in a direction perpendicular to the plane of the paper in the drawings of FIGS. 1a to 1c. FIG. 2 is a view taken looking down on the upper surface of the tissue shown in FIGS. 1a to 1c, and it will be seen that each of the loops formed by the hook 14 and the shoe 11 passes through the preceding such loop. How this is achieved can be understood by imagining the effect of moving the needle forwardly from the position shown in FIG. 1c, with suction reapplied to the slot 2 to suck the tissue into the slot. It will be appreciated that the forward end of the needle will pass through the loop of thread caught between the hook 14 and the shoe 11, carrying a new loop of thread with it. It should be mentioned that to assist this process a small groove can be formed in the upper surface of the shoe, up which the tip of the needle can slide. This enables the needle to pass under the loop of thread already caught between the hook and shoe, without the risk that the needle may simply push the existing loop further up the surface of the shoe. Once the needle has placed the second loop through the first loop the hook 14 is pivoted to allow the first loop to be cast off by pulling on the tail of the thread. The hook 14 is then pivoted downwardly again, so that when the needle is withdrawn the second loop of thead is caught thereby.

As already mentioned, the body 1 is preferably made of a transparent material, so as to make it easier for the operator to see, and hence control, the operation of the machine. The control mechanisms can pass down the channel of an existing endoscope, or the machine can be used independently with a small supervising endoscope passed in parallel with the control channel of the machine.

Figure 3A:
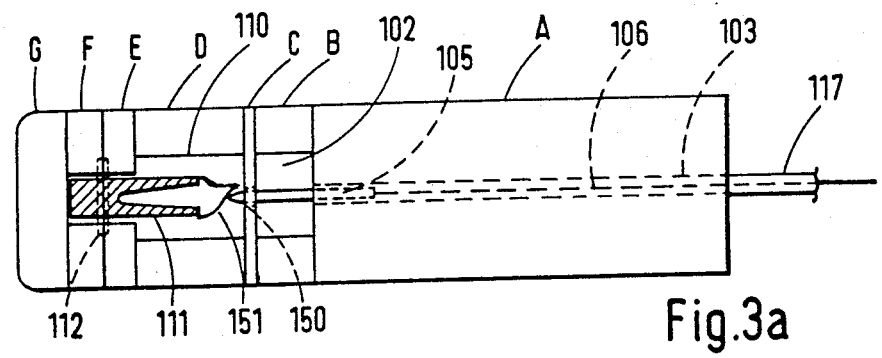
FIGS. 3a and 3b are underplan and side elevational views respectively showing a second embodiment of a sewing machine.
Figure 3B:
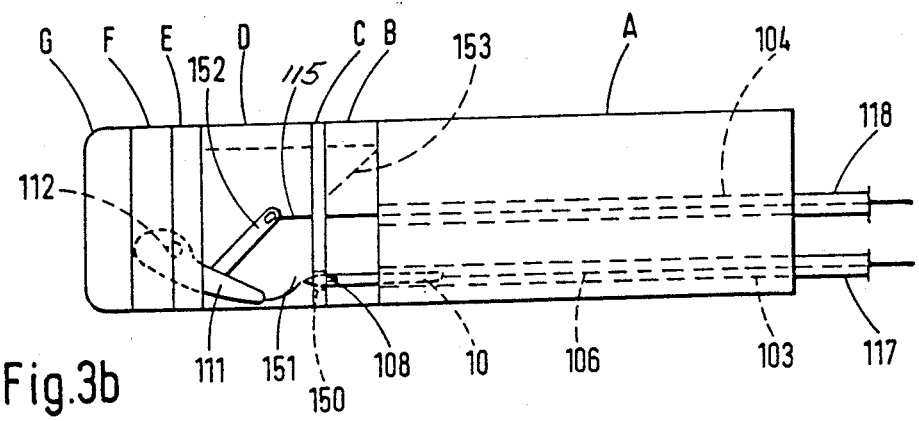

The embodiment shown in FIGS. 3a and 3b is modular in construction, and comprises modules A to G joined face to face and held in position by suitable means, for example, a pair of longitudinally extending bolts passing through aligned bores in the individual modules. In the embodiment illustrated the modules B and D are formed of a transparent material and the remaining modules are not, but others of the modules may be transparent, and indeed it is preferable for some purposes that at least the module A should be transparent.

The module A is the main body portion, and defines longitudinal channels 103 and 104, corresponding to the channels 3 and 4 shown in FIG. 1. The channel 103 receives a needle 105, which is longitudinally slidable therein under the control of a control wire 106. The needle 106 has a head portion in which is formed an eye 108 and a thread to be used in sewing is passed through the eye. The channels 103 and 104 are continuous with corresponding channels 117 and 118 formed in a two-channel endoscope tube, the rest of the endoscope being omitted for simplicity in FIGS. 3a and 3b.

The module B has a slot 102 formed therein, which, as viewed in underplan view, extends across the central region of the module B and which, as viewed in elevation, extends from the top of the module to a location falling just short of the bottom.

The module B is separated by module C, which constitutes a spacer disc and which has an aperture 150 therein through which the needle 105 can pass, from the module D. Module D has a compartment 110 therein which is aligned with slot 102 in module B.

Modules E and F retain a pin 112 on which a U-shaped member 111 is pivotally mounted. The arms of the member 111 each carry a respective resilient wire 151. As can be seen in FIG. 3a, the wires converge towards one another at their tips as viewed in underplan, and, as can be seen in FIG. 3b, the tip portions of the wires are bent upwardly and one of the wires is longer than the other and thus extends further upwards than does the other.

A control wire 115, which passes down the channels 118 and 104 is attached to an arm 152 which is, in turn, rigidly connected to the U-shaped member 111.

The module G provides a curved or bevelled front end to the device, so as to increase the ease with which it can be introduced into a patient.

A source of suction (not shown) is connected to the proximal end of the channel 118 for a purpose which will be described in more detail below and which is basically similar to that for which the source of suction is used in the embodiment of FIG. 1.

The operation of the device of FIGS. 3a and 3b will now be described with reference to FIGS. 4a to 4h. It should be noted that these figures are diagrammatic in character. In each case module G has been omitted, and the modular construction of the remaining portion of the device has not been shown in detail.

The initial position is shown in FIG. 4a with the machine positioned above a layer of tissue 116 in which it is desired to form stitches. Suction is then applied to the slot 102 via the channel 104 to suck into the slot a double layer of tissue, as can be seen in FIG. 4b. The depth and width of the slot 102 controls the amount of tissue which is sucked in. The modular design of this embodiment makes it possible to vary the amount of tissue sucked in, and hence vary the size of the stitches, simply by removing module B and replacing it by a module having a different thickness of depth of slot.

The needle 105 is then forced forwards through the double layer of tissue, as shown in FIG. 4c. The needle carries with it a loop of a thread 109. The needle passes behind the upwardly extending tip portions of both of the wires 151, as viewed in FIG. 4c. The control wire 115 is then pushed leftwards, as shown in FIG. 4c, to cause the U-shaped member 111 to pivot anti-clockwise and thus to cause the outer end of the wires 151 to pass upwardly on the same side of the needle and through the loop of thread carried by the eye of the needle 105. That is, the wires pass between the needle and one of the runs of thread to catch the same. The needle 105 is then withdrawn rightwards whilst the U-shaped member is rotated fully anti-clockwise carrying the thread upwards into the compartment 110. This is shown in FIG. 4d. This last action forms the thread into a large diameter loop. This results from the fact that the wires 151 diverge from one another as considered in a direction running leftwardly from their tips.

The suction applied to the slot 102 is then released and the double layer of tissue, with the thread 109 passing through it, leaves the slot. This is also shown in FIG. 4d.

The machine is then moved with respect to the tissue in any direction to the right of a plane drawn perpendicular to the plane of the paper and passing through the machine. Thus, the machine could be moved rightwardly in a direction parallel to its length, or at any angle less than 90° with respect to the aforesaid direction. The step shown in FIG. 4e is then carried out, that is to say, suction is re-applied and the needle caused to pass through a double layer of tissue at a different point to that where the needle passed through the tissue in step 4c. As can be seen in FIG. 4e, the forward end of the needle passes through the loop of thread already held by the U-shaped member 111, carrying a second loop of thread with it. Once the needle has placed this second loop through the first loop, the U-shaped member is pivoted clockwise, as shown in FIG. 4f. The wires 151, being resilient, are forced apart by the needle and thus pass one on either side of the needle as the U-shaped member 111 travels to the position shown in FIG. 4f, in which it is below the needle. In so doing the wires 151 drop the first loop onto the second loop.

The member 111 is then pivoted anti-clockwise, as shown in FIG. 4g, so as to catch the second loop carried by the eye of the needle. This is shown in FIG. 4g. Both wires 151 at this stage lie against the needle 102 and between the needle 102 and the adjacent portion of the thread 109.

As shown in FIG. 4h, the needle 102 is then withdrawn rightwardly and the member 112 is pivoted further in an anti-clockwise direction, carrying the second loop upwards with it. As also shown in FIG. 4h, the suction is then released to allow the tissue to leave the slot 102.

The above procedure is repeated as many times as are necessary in order to produce the desired number of stitches.

Various modifications may be made to the embodiments described above. One of these is that the machine can be provided with a plurality of slots 2 into each of which a double layer of tissue may be sucked. A single needle can then pass through each of these double layers of tissue, thus making a plurality of stitches in a single operation. Also, it should be understood that the stich forming part of the machine could be modified to correspond to that of any one of a number of conventional sewing machines. For example, the stitching mechanism could be one which uses two threads, rather than one as in the illustrated embodiments.

As mentioned above, the module A is preferably transparent. This is to make it easier for the operator to see, and hence control the operation of the machine. Visibility may further be improved, both in the embodiment of FIGS. 3 and 4 and in the embodiment of FIG. 1, by positioning a mirror in the slot 102 (or slot 2) at 45° to the longitudinal axis of the machine. By way of example this is shown diagrammatically as 153 in FIG. 3b. This enables the user to see the double layer of tissue sucked into the slot 2. A still further improvement can be achieved by extending the endoscope optics right up to the slot 102 (or 2).

Some of the principles utilised in the above sewing machines can be applied with similar effect to the construction of a stapling machine which can also be used in a surgical environment. An embodiment of such a stapling machine is shown in FIGS. 5a to 5c, which show successive steps in its operation.

The stapling machine comprises a body 200 which, if desired, may be of modular construction. The body is preferably wholly or partially of a transparent material. The body defines a cavity 202 into which tissue 216 may be sucked by suction applied through a suction channel 204. Before use, the cavity 202 is pre-loaded with a staple 209. The body also contains a second channel 203 through which extends a wire 206 carrying a piston 205 at its end. The cavity 202 has, in one wall thereof, an anvil plate 260, for a purpose which is described below.

Figure 5A:
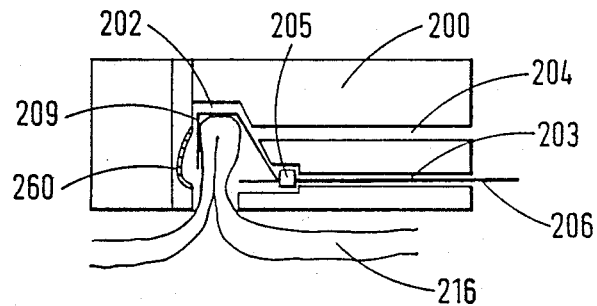
FIGS. 5a to 5c show longitudinal sections through an embodiment of stapling machine according to the present invention, in successive stages of operation.
Figure 5B:
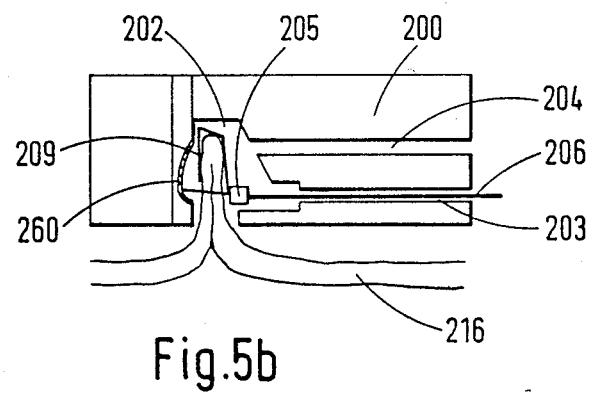
Figure 5C:
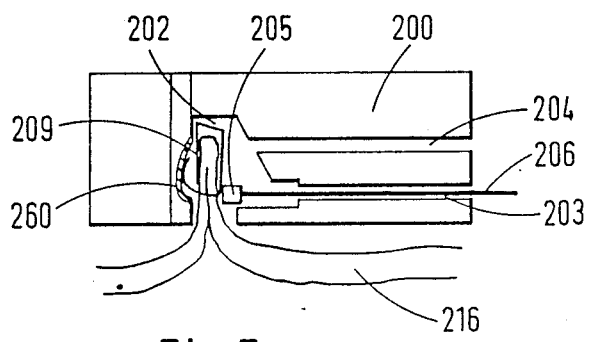

In the starting condition shown in FIG. 5a, the staple 209 comprises four consecutive rectilinear sections, namely a first upwardly extending section, a second horizontally extending section, a third diagonally downwardly extending section, and a fourth section, which is parallel to the second section, and has its free end directed towards the first section. In the condition shown in FIG. 5a suction has been applied to the channel 204 to suck into it a double layer of tissue 216. As shown in FIG. 5b the next step is for the piston 205 to be moved leftwardly by means of the wire 206, thus driving the fourth sections of the staple through the double layer of tissue so that its tip comes into contact with the anvil 260, and simultaneously deforming the remaining sections of the staple. As shown in FIG. 5c, further leftward movement of the piston 206 causes the tip of the staple to ride along the anvil 206, thus twisting it around the first section of the staple and locking the staple so that it exerts a compressive force on the tissue held by it. The illustrated embodiment shows only a single staple. However, the machine may carry a plurality of staples connected side by side as in the case of staples used, for example, in stationery applications. In this case, the row of staples is biassed, for example, by a spring exerting a force perpendicular to the plane of the paper as viewed in FIG. 5, a stop being provided to retain the row of staples in the correct position against the biassing force.

FIGS. 6a to 6f show, in part, a further embodiment according to the present invention. The construction of this embodiment will become apparent from the following description of how it operates. This embodiment includes two needles 20 and 30. Before the stage shown in FIG. 6a, the needles are withdrawn such that their tips are separated by about 5 mm. Then, as shown in FIG. 6a, the first needle 20 is passed obliquely through the tissue 16, as indicated by the arrow. The needle 20 has a pair of opposed barbs 21 separated by a slot 22. The slot 22 provides access to an opening 23. A loop of thread 24 is carried forwardly by the needle. The tissue 16 is held in place by suction applied to a tube 25. Only the end of the tube 25 is visible in the figures. The proximal end of the needle 20 is guided for rectilinear movement in a bush (not shown).

As shown in FIG. 6b, once the needle 20 has been passed through the tissue to the full extent which is required an identical needle 30 is inserted through the tissue at a location remote from that at which the needle 20 passed through the tissue. The needle 30 is angled oppositely to the needle 20 so that, as shown in FIG. 6b, its path of travel intersects that of the needle 20. At this stage the needle 30 carries no thread. Furthermore, the needle 30 is rotated by 90° about its longitudinal axis compared to the needle 20. The needle 30 has a slot 32, corresponding to slot 22 of needle 20, and barbs 31, corresponding to barbs 21 of needle 20. As shown in FIG. 6b, the needle 30 passes between the needle 20 and the loop of thread 24 carried by the needle 20. To assist in this the needle 20 is provided with a depression 26 which is obscured in FIG. 6 but which can be seen in FIG. 6c.

In the position illustrated in FIG. 6b, the slot 32 is located immediately below the thread 24. This causes the thread 24 to pass through the slot 32 and thus causes it to be caught by the needle 30.

As shown in FIG. 6c, the needle 30 is then partially withdrawn, and as it does so it pulls the loop of thread 24 with it. As shown in FIG. 6d, when the needle 20 is then partially withdrawn the thread 24 is freed from the needle 20 and held only by the needle 30. Further withdrawal of both needles 20 and 30 to a position where both pass out of the tissue 16 causes the situation to be reached which is shown in FIG. 6e where a stitch has been formed.

Figure 8:
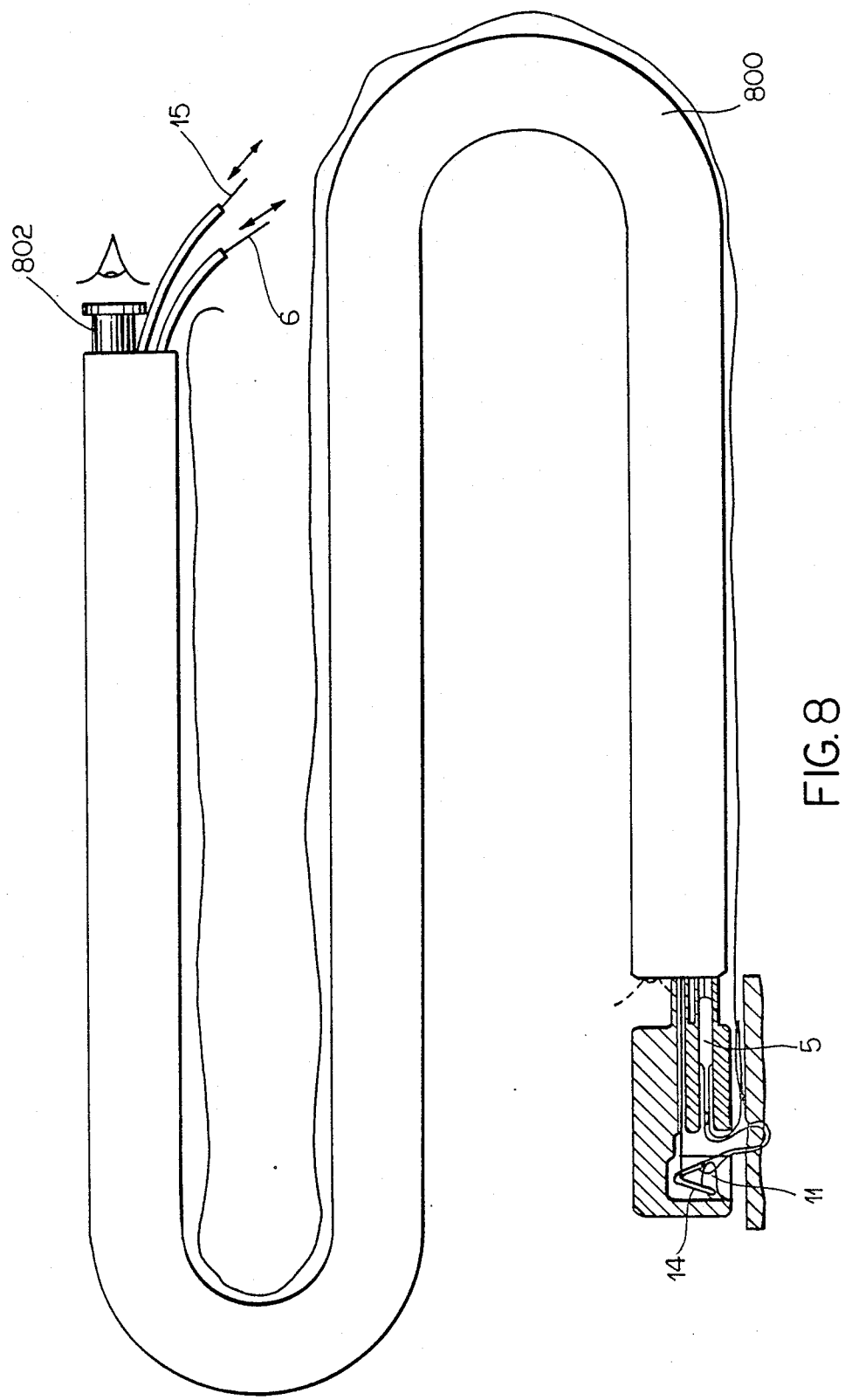
FIG. 8 is a diagrammatic view showing the machine of FIG. 1 mounted on the end of an endoscope.

Each of the needles 20 and 30 is then rotated by 90° about its own axis, so that needle 20 assumes the orientation and function which was previously that of needle 30 and needle 30 assumes the orientation and function which was previously that of needle 20. The above described process is then repeated with the functions of the needles 20 and 30 interchanged. This procedure is continued as many times as are necessary to produce the required number of stitches. FIG. 8 illustrates the use of a conventional endoscope 800 in connection with the sewing machine shown in FIG. 1. The endoscope includes an eyepiece 802. Additionally, the control wires 6 and 15 extend through the endoscope.

The use of an endoscopic sewing machine according to the present invention gives rise to a requirement for a suitable means for securing knots and cutting thread. Secure knots are essential for surgery, and tying knots and cutting thread by remote control in confined spaces, as is necessary in conjunction with the use of the endoscopic sewing machines described above, imposes special requirements. Some ways of satisfying these requirements are therefore mentioned below.

One method of tying a knot is as follows. A washer having a central hole, the diameter of which is a clearance fit on the thread to be fastened is fed onto the thread. The thread is tied as a half-hitch around a pin pressed through the two walls of the end of a strong but flexible catheter tube. By holding the tail of the thread and pushing on the tube the half-hitch and washer in front of it may be run forward. When the desired position has been reached, the pin is removed remotely by pulling on a wire to which it is attached and which runs along the outside of the catheter. In another method of fastening the thread, a plastic washer is run over the thread down the endoscope channel. Plastic is preferred to metal because it is resistant to acid digestion. A compressible tapered sleeve is passed over the thread and a rammer bears down on the sleeve, distorting it tightly over the thread and against the washer while pull is exerted on the thread. Yet another method of fastening the thread uses a Z-shaped plastic strip having holes for the thread in the three limps of the Z-shape. There is a V-shaped slit cut in the proximal hole. The thread is run through all the three holes of the Z-shaped strip which is pushed through the endoscope channel. A pushing device compresses and folds the Z-shaped strip like a flattened concertina against the tissue. This tightens on the thread forcing it into the narrow V-shaped slit which holds the thread securely.

Figure 7A:
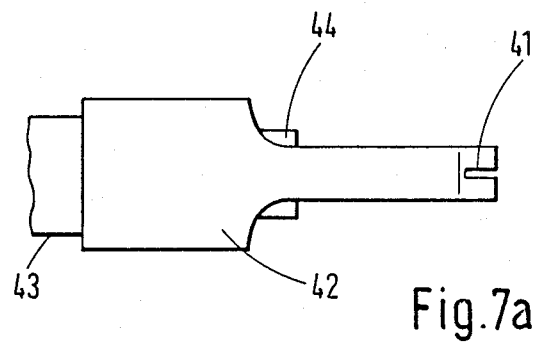
FIGS. 7a to 7c are, respectively, a plan view, a vertical section and an end view of a thread guillotine for use in conjunction with the sewing machine of the present invention.
Figure 7B:
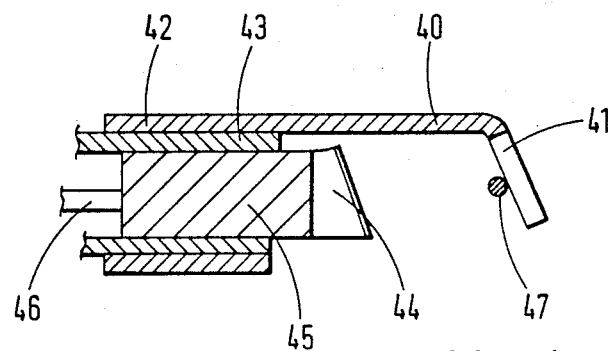
Figure 7C:
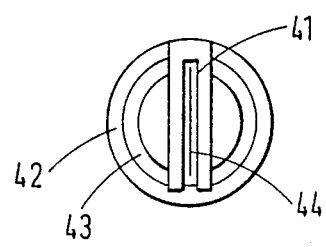

FIG. 7 shows a thread guillotine for endoscopic use. This comprises a crooked leg 40 with a slit 41 cut centrally along its length at one end thereof. The leg 40 is formed on the end of a metal tube 42 which is pressed over the end of a small diameter plastic catheter tube 43. A knife blade 44 is held in a piston 45 which is free to move axially in the bore of the tube 43. A wire 46 attached to the piston 45 and running through the bore of the tube 43 controls the movement of the blade when pushed forward. The blade 44 passes through the slot 41 in the crooked leg, thereby acting as a guillotine to sever the thread 47.

Finally, mention may be made of a suction overtube to facilitate sewing down an endoscope by means of a machine according to the present invention, or indeed by some other means. The overtube envisaged is a transparent flexible tube which fits loosely over the endoscope. An air-tight seal is made with an elastic sleeve between the overtube and the endoscope. A hole of specific dimensions is cut in the extreme end or in the side of the overtube distally. Air is sucked from the overtube such that tissue to be sewed protrudes into the overtube where it is held in a conformation which enables the tissue to be readily transfixed by a threaded needle.

It is to be understood that the various devices described above as being ancillary to the sewing machine according to the present invention are believed to be novel in their own right and form independent aspects of the present invention.

We claim:

1. A sewing machine for forming stitches in a substrate, comprising thread-carrying means for passing a thread into the substrate from one side thereof at a first location and for withdrawing the thread from the substrate at a second location spaced from the first location, said means being being remotely operable solely from the said one side of the substrate, means defining a slot open toward the substrate, a channel communicating with said slot to provide suction thereto for drawing a double layer of substrate into the slot, the thread-carrying means being disposed for movement from a retracted position to an extended position, in which movement that carries a loop of the thread into and through the said double layer, and further comprising means for catching the said loop after it has passed through the double layer of substrate and holding the said loop while the thread-carrying means is withdrawn to the retracted position.

2. A machine according to claim 1, wherein the catching means is movable from a catching position to a position in which the loop caught thereby is positioned so that subsequent movement of the thread-carrying means from said retracted position to said extended position carries a further loop of thread through the previously caught loop.

3. A machine according to claim 2, comprising a block having distal and proximal ends, the block defining a compartment adjacent the distal end housing the catching means, said slot being defined in the block on the proximal side of the compartment, said suction-supplying channel being defined in the block on the proximal side of the slot, a further channel being defined on the proximal side of the slot and communicating with the slot, said thread-carrying means being slidably received therein for movement between said retracted position, in which the thread-carrying means is substantially wholly within said further channel, and said extended position, in which the thread-carrying means extends across said slot into said compartment.

4. A machine according to claim 3, wherein control means for controlling the catching means extend through the suction-supplying channel and across said slot into said compartment to connect with the catching means.

5. A machine according to claim 4, wherein said control means comprises a flexible wire, and wherein the machine further comprises a further flexible wire for moving the thread-carrying means between the retracted and extended positions.

6. A machine according to claim 4, wherein the catching means comprises a shoe resiliently mounted in the compartment for pivotal movement about an axis transverse to the length of the block, and a hook pivotally mounted at one end on the shoe and movable by said control means between a position in which the other end thereof is in contact with the shoe and a position in which there is no such contact.

7. A machine according to claim 4, wherein the catching means comprises a pair of arms defining a U, the U-shaped member being mounted in the compartment for pivotal movement about an axis transverse to the length of the block and a pair of resilient members each extending from a respective one of said arms, the resilient members converging towards one another adjacent the outward ends thereof, the U-shaped member being movable by said control means between an outward position in which, when the thread-carrying means is in its extended position both resilient members are closely adjacent the thread-carrying means on the same side thereof, and an inward position in which the resilient members are located inwardly of the thread-carrying means.

8. A machine according to claim 3, wherein the block is formed of a plurality of disconnectible modules located face to face, one of said modules being a module defining said slot.

9. A machine according to claim 3, wherein proximally of the slot the block is transparent.

10. A machine according to claim 3, further comprising mirror located in the said slot and angled with respect to a line extending between the proximal and distal ends of the block.

11. A sewing machine for forming stitches in a substrate, comprising thread-carrying means for passing a thread into the substrate from one side thereof at a first location and for withdrawing the thread from the substrate at a second location spaced from the first location, the said means being remotely operable solely from the said one side of the substrate, the machine being mounted on the end of an endoscope.

* * * * *